(12) United States Patent
Seipp et al.

(10) Patent No.: US 6,509,368 B1
(45) Date of Patent: Jan. 21, 2003

(54) USE OF CATECHOL DERIVATIVES AS PROTEINASE INHIBITORS

(75) Inventors: Ulrich Seipp, Aachen (DE); Oswald Zimmer, Wuerselen (DE); Wolfgang Strassburger, Wuerselen (DE); Johannes Schneider, Stolberg (DE); Stephan Wnendt, Aachen (DE); Norbert Ulbrich, Potsdam (DE); Heide Hecker-Kia, Berlin (DE); Bernd Zimmermann, Berlin (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/806,466
(22) PCT Filed: Sep. 23, 1999
(86) PCT No.: PCT/EP99/07068
§ 371 (c)(1), (2), (4) Date: Jul. 13, 2001
(87) PCT Pub. No.: WO00/19989
PCT Pub. Date: Apr. 13, 2000

(30) Foreign Application Priority Data

Oct. 2, 1998 (DE) .......................... 198 45 372

(51) Int. Cl.$^7$ .................... A61K 31/415; A61K 31/045; A61K 31/05; A61K 31/445
(52) U.S. Cl. ........................ 514/406; 514/407; 514/724; 514/732; 514/316; 514/319; 514/321
(58) Field of Search ................... 514/406, 407, 514/732, 724, 319, 316, 321

(56) References Cited

U.S. PATENT DOCUMENTS 4,760,087 A 7/1988 Zimmer et al.
4,959,391 A 9/1990 Zimmer et al.

FOREIGN PATENT DOCUMENTS

| EP | 202529 B1 | 12/1989 |
|---|---|---|
| WO | WO 88/01509 A1 * | 3/1988 |
| WO | WO 96/31206 A2 * | 10/1996 |
| WO | WO 97/11692 A2 * | 4/1997 |
| WO | WO 9908672 A1 * | 2/1999 |

* cited by examiner

Primary Examiner—Zohreh Fay
Assistant Examiner—Brian-Yong S. Kwon
(74) Attorney, Agent, or Firm—Crowell & Moring LLP

(57) ABSTRACT

Use of catechol derivatives of the general formula I

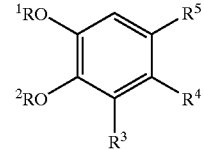

wherein $R^1$ to $R^5$ are as defined according to claim 1, as protease inhibitors.

17 Claims, No Drawings

USE OF CATECHOL DERIVATIVES AS PROTEINASE INHIBITORS

This application is a 371 of PCT/EP99107068 Sep. 3, 1999.

The invention relates to the use of selected catechol derivatives as protease inhibitors, and to their use in the treatment of diseases in whose pathogenesis elastase and/or metalloproteases are involved.

Metalloproteases and the serine protease elastase play a central role in the formation and progression of inflammatory diseases in the human body, such as rheumatoid arthritis, periodontitis, the reaction of the skin to UV radiation, as well as primarily non-inflammatory diseases, such as the formation of arteriosclerotic plaques, the mobilisation of tumour cells and the formation of metastases, osteoporosis and arthrosis. The function of the metalloproteases in the course of those processes consists on the one hand in breaking down matrix tissue and on the other hand in activating proinflammatory precursor proteins.

The known protease inhibitors are generally complex molecules which are used for the inhibition of metalloproteases. They include, in addition to tetracycline derivatives, for the most part the peptidomimetics (Beckett et al., Drug Discovery Today, (1996), p. 16–26). This gives rise to the problem of limited oral availability for the peptidomimetics, since those substances are digested by relatively unspecific peptidases in the gastro-intestinal tract. The compounds of the general formula I are known, for example, from EP-A-0 202 529 and WO 96/31206 as lipoxygenase inhibitors and antihistamines and from WO 82/03729 as adjuvants for the modification of electrodes.

The object of the present invention was to make available compounds which are used as protease inhibitors for the treatment of diseases in whose pathogenesis metalloproteases and/or elastase are involved.

It has now been found that the requirements made of the compounds were fulfilled by selected catechol derivatives of the general formula I. The compounds are distinguished by pronounced inhibition of metalloprotease and/or elastase activity.

Accordingly, the invention provides selected catechol compounds of the general formula I

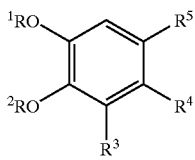

wherein
$R^1$ represents H, aryl-heterocyclyl, $C_{1-16}$-alkyl, aryl, CHO, CON(CH$_3$)$_2$, COCH$_3$, CO-tert.-butyl, heterocyclyl or $C_{2-16}$-alkenyl;
$R^2$ represents H, aryl-heterocyclyl, $C_{1-16}$-alkyl, aryl, CHO, CON(CH$_3$)$_2$, COCH$_3$, CO-tert.-butyl, heterocyclyl or $C_{2-16}$-alkenyl;
$R^3$ represents H, OH, $C_{2-16}$-alkoxy or $C_{2-6}$-alkenyl-COO-$C_{1-6}$-alkyl;
$R^4$ represents aryl, —CH=CH-aryl, H, unsubstituted and/or OH—, NH$_2$— or halo-substituted $C_{2-16}$-mono- or di-alkynyl, heterocyclyl, —C(O)-heterocyclyl, $C_{1-8}$-alkyl, or $R^3$ and
$R^4$, together with the carbon atoms of the aromatic ring, form a 4- to 6-membered saturated or partially unsaturated cyclic hydrocarbon ring; and $R^5$ represents aryl, —CH=CH-aryl, H, unsubstituted and/or OH—, NH$_2$— or halo-substituted $C_{2-16}$-mono- or di-alkynyl, heterocyclyl, —C(O)-heterocyclyl, $C_{1-8}$-alkyl, or $R^4$ and $R^5$, together with the carbon atoms of the aromatic ring, form a 4- to 6-membered saturated or partially unsaturated cyclic hydrocarbon ring;

in the form of bases or pharmaceutically acceptable salts, which are used as protease inhibitors in the treatment of diseases in whose pathogenesis elastase and/or metalloproteases are involved.

In the present invention, the expression "$C_{1-6}$-alkyl" means straight-chained or branched hydrocarbons having from 1 to 16 carbon atoms. There may be mentioned by way of examples methyl, ethyl, propyl, n-butyl, sec.-butyl, n-pentyl, neopentyl, n-hexyl, n-heptyl, 2,3,4-trimethyl-heptyl, 2,2,3,4,5,5,6-heptamethyl-octyl, n-nonyl, 2,6-diethyl-3,4,5-trimethyl-decanyl, n-undecanyl, n-dodecanyl and 3-ethyl-4-methyl-dodecanyl.

Within the scope of the present invention, the expression "$C_{1-6}$-alkoxy" means straight-chained or branched hydrocarbons having from 1 to 16 carbon atoms, as defined above, which are bonded via the oxygen atom.

The expressions "$C_{2-6}$-alkenyl" and "$C_{2-16}$-alkenyl" in the present invention mean straight-chained or branched hydrocarbons having from 2 to 6 or from 2 to 16 carbon atoms, respectively, as defined above, which additionally contain a free double bond within the carbon chain.

Within the scope of the present invention, the expression "$C_{2-16}$-mono- or di-alkynyl" means straight-chained or branched hydrocarbons having from 2 to 16 carbon atoms, as defined above, which additionally contain one or two free triple bonds within the carbon chain. The hydrocarbon radical may additionally contain substituents from the group OH, NH$_2$ and/or halogen.

The expression "aryl" within the scope of the present invention means phenyls or naphthyls which are unsubstituted or mono- or poly-substituted by OH, F, Cl, CF$_3$, $C_{1-6}$-alkyl, $C_{1-16}$-alkoxy, $C_{3-7}$-cycloalkyl, $C_{2-16}$-alkenyl, heterocyclyl or by phenyl. The heterocyclyl or phenyl radicals may optionally be condensed on.

Within the scope of the present invention, the expression "heterocyclyl" means 5- or 6-membered saturated or unsaturated heterocyclic compounds which contain 1 or 2 hetero atoms from the group nitrogen, oxygen and/or sulfur, are optionally provided with a condensed on aryl system, and are unsubstituted or mono- or poly-substituted by OH, F, Cl, CF$_3$, $C_{,1-16}$-alkyl, $C_{1-6}$-alkoxy, $C_{2-16}$-alkenyls, mono- or di-$C_{2-16}$-alkynyls, $C_{2-16}$-saturated or unsaturated carboxylic acids or carboxylic acid esters having from 2 to 16 carbon atoms for the hydrocarbon part of the carboxylic acid and from 1 to 6 carbon atoms for the hydrocarbon part in the ester, by heterocyclyl or by phenyl.

Examples of saturated heterocyclyls which may be mentioned are 1,4-dioxane, tetrahydrofuran, pyrrolidine, oxazolidine and 1,4-thioxane.

From the group of the unsaturated heterocyclyls there may be mentioned by way of examples furan, thiophene, pyridine, pyrimidine, pyrazole, thiopyran, pyran, thiazole, oxazole, isoxazole, pyridazine, pyrazine, quinoline, isoquinoline, phthalazine and quinazoline.

Within the scope of the present invention, the term "aryl-heterocyclyl" is to be understood as meaning "aryl" and "heterocyclyl" as defined above, which are bonded to one another via a single bond.

Preference is given to compounds in which the radicals $R^1$ and $R^2$ represent hydrogen and the radicals $R^3$ to $R^5$ are as defined above.

Preference is given to compounds selected from the group:

5,6,7-trihydroxy-3,4-dihydronaphthalene-2-carboxylic acid methyl ester;
4-nonyloxy-1,2-benzene diol;
(3,4-dihydroxy-phenyl)(5-phenyl-1H-pyrazol-3-yl)-methanone;
4-(2-naphth-2-yl-vinyl)-1,2-benzene diol;
3-(6-hept-1-ynyl-2,3-dihydroxy-phenyl)-acrylic acid methyl ester; and
4-(11-hydroxy-undeca-1,9-diynyl)-1,2-benzene diol.

Example 1: 5,6,7-trihydroxy-3,4-dihydronaphthalene-2-carboxylic acid methyl ester;
Example 2: 3-(6-hept-1-ynyl-2,3-dihydroxy-phenyl)-acrylic acid methyl ester;
Example 3: 4-nonyloxy-1,2-benzene diol;
Example 4: 4-(11-hydroxy-undeca-1,9-diynyl)-1,2-benzene diol;
Example 5: 4-(2-naphth-2-yl-vinyl)-1,2-benzene diol;
Example 6: (3,4-dihydroxy-phenyl)(5-phenyl-1H-pyrazol-3-yl)-methanone.

TABLE 1

Action on metalloproteases and elastase in vitro

| Compound | Human fibroblast collagenase (MMP-1): $IC_{50}$ value ($\mu M$) or % inhibition at concentration | Stromelysin-1 (MMP-3) $IC_{50}$ value ($\mu M$) or % inhibition at concentration | Human leucocyte collagenase (MMP-8): $IC_{50}$ value ($\mu M$) or % inhibition at concentration | Human gelatinase B (MMP-9): $IC_{50}$ value ($\mu M$) | Human elastase $IC_{50}$ value ($\mu M$) |
|---|---|---|---|---|---|
| Example 1 | — | 850 | 60 | 72 | 5.5 |
| Example 2 | — | — | 173 | — | 2.0 |
| Example 3 | — | 320 | 40% (100 $\mu M$) | — | 1.6 |
| Example 4 | — | — | — | — | 55 |
| Example 5 | 40% (100 $\mu M$) | 22% (100 $\mu M$) | 100 | 32 | 0.125 |

The compounds of the general formula I according to the invention are used in the treatment of diseases from the group rheumatoid arthritis, periodontitis, arteriosclerotic plaques, osteoporosis, arthrosis, metastasisation and neoangiogenesis of tumours, ulceration of the cornea and reactions of the skin to UV radiation.

The compounds of the general formula I are used especially in the treatment of rheumatoid arthritis, periodontitis, arteriosclerotic plaques, osteoporosis, arthrosis, and metastasisation and neoangiogenesis of tumours.

The catechol derivatives of the general formula I are preferably used in the treatment of osteoporosis, arteriosclerotic plaques and arthrosis.

EXAMPLES

The Examples which follow served to demonstrate the activity according to the invention of the catechol compounds of the general formula I on matrix metallo-proteases (MMPs) and elastase.

To that end, experiments were carried out using various matrix metalloproteases from the group human fibroblast collagenase (MMP-1), stromelysin-1 (MMP-3), human leucocyte collagenase (MMP-8) and human gelatinase B (MMP-9), and on human elastase, which proved that inhibition is brought about by the protease inhibitors according to the invention. The experiments were carried out in vitro using purified human enzymes. The enzyme substrates used were substrates to be measured by photometry or fluorometry. The results have been summarised in Table 1 below. The data proved that the compounds of the general formula I have metalloprotease-inhibiting properties. The inhibition of elastase has also been demonstrated. The compounds showed variable activity in the inhibition of elastase.

The following compounds were used in the Examples below in the sequence specified:

As well as inhibiting metalloproteases, the compounds of the general formula I also exhibited inhibition as regards elastase (Table 1).

In a further in vitro experiment, the effectiveness of the compounds as regards inflammatory diseases was tested in an organoid model of cartilage formation. For that model, mesenchymal cells from the limb buds of murine embryos were placed in cell culture. In the cell culture, the cells formed an extracellular matrix corresponding to joint cartilage. Mineralisation of the extracellular matrix was induced by addition of β-glycerophosphate. Cartilage formation and mineralisation were inhibited by addition of bacterial lipopolysaccharide (LPS) as inflammation mediator. The effect of the compounds on the LPS-induced impairment of mineralisation was examined by measuring the calcium content of the extracellular matrix by flame photometry after culturing for 14 days. The effect on cartilage formation was demonstrated by checking the proteoglycan content of the extracellular matrix using the dyestuff Alcian blue after a treatment period of from 4 to 16 days.

TABLE 2

Effect of compounds having in vitro activity in the organoid model

| Compound | Chondrocytes: Mineralisation in the presence of LPS; action at a concentration of 10 $\mu m$ |
|---|---|
| Example 1 | +42% |
| Example 2 | +38% |
| Example 3 | +43% |
| Example 4 | +12% |
| Example 5 | +81% |
| Example 6 | +17% |

The values indicate the percentage increase in mineralisation in comparison with the LPS-treated culture.

The results shown in Table 2 demonstrated that the LPS-induced reductions in matrix mineralisation were antagonised by means of the compounds according to the invention. An increased Alcian blue binding for the proteoglycan content of the extracellular matrix served as a measure of the chondroprotective action. The compounds stimulated preservation of the extracellular matrix not only in the presence but also in the absence of LPS. The increase in Alcian blue binding was concentration-dependent. Some compounds showed over the course of time that they induced a massive chondroprotective effect by inhibiting breakdown. That effect was accompanied by a marked inhibition of the release of prostaglandin $E_2$ ($PGE_2$) into the cell culture medium of the organoid model. Increased $PGE_2$ concentrations have also been found in the synovial fluid of arthritic patients. Prostaglandin $E_2$ ($PGE_2$) is a known product of arachidonic acid metabolism from the cyclooxygenase pathway. That prostaglandin increases the pronociceptive action of bradykinin, causes vasodilation and has an activity promoting oedema.

In a further test, the surprising results of the in vitro Example and the findings of the murine organoid model were verified using the example of rheumatoid arthritis. The catechol derivatives were tested in a cell culture of human synovial fibroblasts. The cell material used for the experiments originated from arthritic knee joints.

The fibroblast cultures were treated with the various stimuli lipopolysaccharide (LPS), interleukin-1 (IL-1) and a neuropeptide, substance P. Lipopolysaccharide and interleukin-1 are pro-inflammatory mediators. Substance P is a neurotransmitter of the afferent neurones which is involved in inflammatory processes and the processing of pain (N. Otsuka and K. Yoshioka, The Am. Physiol. Soc., Vol. 73, No. 2, April 1993, 229–308). The release of interleukin-6 (IL-6), an inflammation mediator, and the activity of the secreted metalloproteases were used as the measuring parameters. The-release of IL-6 was inhibited by the catechol derivatives according to the invention.

The matrix metalloprotease activity in the cell culture medium was measured using a fluorogenic substance (Knight CG et al. (1992), FEBS Lett. 296, 263). The proteolytic activity of the samples without addition of catechol derivatives of the general formula I was regarded as being 100%. The cell culture media treated with compounds at a concentration of ($10^{-5}$ M) exhibited inhibition of the proteolytic activity independently of the in vitro activation of the pro-enzymes.

After incubation with trypsin and trypsin inhibitor (in this system, mainly the interstitial collagenase, MMP-1, was activated), inhibition of 90% was observed in the case of some compounds, while in the case of activation by 4-aminophenylmercury acetate (APMA), which activated mainly gelatinase A, only slight inhibition was initiated. The stromelysin-1 activity (MMP-3), measured using a specific fluorogenic substrate (Nagase et al. (1994), J. Bid. Chem. 269, 20952), was inhibited by 85% as compared with the untreated control medium.

Stimulation of synovial fibroblasts by lipopolysaccharides, IL-1 and the neuropeptide substance P led in the presence of catechol derivatives according to the invention to a reduced matrix metalloprotease activity.

Following lipopolysaccharide stimulation, the matrix metalloprotease activity (MMPs) activatable by 4-aminophenylmercury acetate (APMA), i.e. gelatinase A in this case, was inhibited only slightly, while the trypsin-activatable matrix metalloprotease activity (MMPs), i.e. stromelysin-1 (MMP-3), was inhibited.

The inhibitory action of the compounds on the matrix metalloprotease activities of IL-1-stimulated synovial fibroblasts could likewise be demonstrated.

The APMA-activatable matrix metalloprotease activity, i.e. gelatinase A, was not inhibited following stimulation by the neuropeptide substance P, while the trypsin-activatable matrix metalloproteinases, i.e. mainly interstitial collagenase and stromelysin-1, were inhibited by 75%.

What is claimed is:

1. A method of treating a disease state selected from the group consisting of rheumatoid arthritis, periodontitis, arteriosclerotic plaques, osteoporosis, arthrosis, metastasis and neoangiogenesis of tumors, ulceration of the cornea and reactions of the skin to UV radiation in a mammal, said method comprising administering to said mammal an effective protease inhibiting amount of a catechol derivative corresponding to formula I:

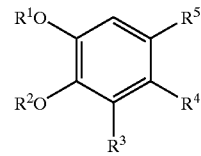

wherein
$R^1$ represents H, aryl-heterocyclyl, $C_{1-16}$-alkyl, aryl, CHO, CON(CH$_3$)$_2$, COCH$_3$, CO-tert.-butyl, heterocyclyl or $C_{2-16}$-alkenyl;
$R^2$ represents H, aryl-heterocyclyl, $C_{1-16}$-alkyl, aryl, CHO, CON(CH$_3$)$_2$, COCH$_3$, CO-tert.-butyl, heterocyclyl or $C_{2-16}$-alkenyl;
$R^3$ represents H, OH, $C_{2-16}$-alkoxy or $C_{2-6}$-alkenyl-COO-$C_{1-6}$-alkyl;
$R^4$ represents aryl, —CH=CH-naphthyl, unsubstituted and/or OH—, NH$_2$— or halo-substituted $C_{2-16}$-mono- or di-alkynyl, —C(O)-heterocyclyl, or $R^3$ and $R^4$ together with the carbon atoms of the aromatic ring to which they are bound form a 4- to 6-membered saturated or partially unsaturated cyclic hydrocarbon ring; and
$R^5$ represents aryl, —CH=CH-aryl, H, unsubstituted and/or OH—, NH$_2$— or halo-substituted $C_{2-16}$-mono- or di-alkynyl, heterocyclyl, —C(O)-heterocyclyl, $C_{1-8}$-alkyl, or $R^4$ and $R^5$ together with the carbon atoms of the aromatic ring to which they are bound form a 4- to 6-membered saturated or partially unsaturated cyclic hydrocarbon ring; or a pharmaceutically acceptable salt thereof.

2. A method according to claim wherein $R^1$ and $R^2$ represent hydrogen.

3. A method of treating a disease state selected from the group consisting of rheumatoid arthritis, periodontitis, arteriosclerotic plaques, osteoporosis, arthrosis, metastasis and neoangiogenesis of tumors, ulceration of the cornea and reactions of the skin to UV radiation in a mammal, said method comprising administering to said mammal an effective protease inhibiting amount of a catechol derivative is selected from the group consisting of:
5,6,7-trihydroxy-3,4-dihydronaphthalene-2-carboxylic acid methyl ester;
4-nonyloxy-1,2-benzene diol;
(3,4-dihydroxy-phenyl)(5-phenyl-1H-pyrazol-3-yl)-methanone;
4-(2-naphth-2-yl-vinyl)-1,2-benzene diol;
3-(6-hept-1-ynyl-2,3-dihydroxy-phenyl)-acrylic acid methyl ester; and 4-(11-hydroxy-undeca-1,9-diynyl)-1,2-benzene diol, or a pharmaceutically acceptable salt thereof.

4. A method according to claim 1, wherein said disease state is selected from the group consisting of rheumatoid arthritis, periodontitis, arteriosclerotic plaques, osteoporosis, arthrosis, metastasis and neoangiogenesis of tumors.

5. A method according to claim 1, wherein said catechol derivative is 4-(2-naphth-2-yl-vinyl)-1,2-benzene diol and said disease state is selected from the group consisting of rheumatoid arthritis, periodontitis, osteoporosis, arterio sclerotic plaques, arthrosis, metastasis and neoangiogenesis of tumors.

6. A method of treating a disease state selected from the group consisting of rheumatoid arthritis, periodontitis, arteriosclerotic plaques, osteoporosis, arthrosis, metastasis and neoangiogenesis of tumors, ulceration of the cornea and reactions of the skin to UV radiation in a mammal, said method comprising administering to said mammal an effective protease inhibiting amount of a catechol derivative corresponding to formula I:

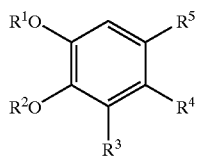

wherein
$R^1$ represents H or $C_{1-16}$-alkyl;
$R^2$ represents H or $C_{1-16}$-alkyl;
$R^3$ represents H, OH or $C_{2-16}$-alkoxy;
$R^4$ represents —CH=CH-naphthyl, unsubstituted and/or OH—, $NH_2$—or halo-substituted $C_{2-16}$-mono- or di-alkynyl, or —C(O)-heterocyclyl; and
$R^5$ represents H; or $R^4$ and $R^5$ together with the carbon atoms of the aromatic ring to which they are bound form a 4- to 6-membered saturated or partially unsaturated cyclic hydrocarbon ring;

or a pharmaceutically acceptable salt thereof.

7. A method according to claim 6, wherein $R^1$ and $R^2$ represent hydrogen.

8. A method according to claim 7, wherein $R^4$ represents —CH=CH-naphthyl.

9. A method according to claim 8, wherein $R^4$ represents —CH=CH-naphth-2-yl.

10. A method according to claim 9, wherein said catechol derivative comprises 4-(2-naphth-2-yl-vinyl)-1,2-benzene diol.

11. A method according to claim 7, wherein $R^4$ and $R^5$ together with the carbon atoms of the aromatic ring to which they are bound form a 6-membered partially unsaturated hydrocarbon ring.

12. A method according to claim 7, wherein $R^4$ represents a C(O)-pyrazolyl group.

13. A method according to claim 12, wherein said C(O)-pyrazolyl group is substituted by phenyl.

14. A method according to claim 13, wherein said catechol derivative comprises (3,4-dihydroxy-phenyl)(5-phenyl-1H-pyrazol-3-yl)-methanone.

15. A method according to claim 7, wherein $R^4$ represents an unsubstituted $C_{2-16}$-monoalkynyl group.

16. A method according to claim 7, wherein $R^4$ represents an OH-substituted $C_{2-16}$-dialkynyl group.

17. A method according to claim 16, wherein said catechol derivative comprises 4-(11-hydroxy-undeca-1,9-diynyl)-1,2-benzene diol.

* * * * *